United States Patent [19]
Hill et al.

[11] Patent Number: 5,576,425
[45] Date of Patent: Nov. 19, 1996

[54] PROCESS FOR THE DIRECT PRODUCTION OF ALKYL GLYCOSIDES

[75] Inventors: Karlheinz Hill, Erkrath; Manfred Biermann, Muelheim; Henry Rossmaier; Rainer Eskuchen, both of Duesseldorf; Willi Wuest, Ratingen; Josef Wollmann, Herzogenrath; Andreas Bruns, Langenfeld; Guenter Hellmann, Hilden; Karl-Heinz Ott, Erkrath; Walter Winkle, Monheim; Klaus Wollmann, Haan, all of Germany

[73] Assignee: Henkel Kommanditgesellschaft auf Aktien, Duesseldorf, Germany

[21] Appl. No.: 279,673

[22] Filed: Jul. 25, 1994

Related U.S. Application Data

[63] Continuation of Ser. No. 112,838, Aug. 26, 1993, abandoned, which is a continuation of Ser. No. 671,733, Jun. 5, 1991, abandoned.

[30] Foreign Application Priority Data

Oct. 5, 1988 [DE] Germany ............... 38 33 780.0

[51] Int. Cl.⁶ ............... C07G 3/00; C07H 1/00; C07H 15/04

[52] U.S. Cl. ............... 536/18.6; 536/18.5; 536/120; 536/124

[58] Field of Search ............... 536/18.6, 18.5, 536/120, 124

[56] References Cited

U.S. PATENT DOCUMENTS

| | | | |
|---|---|---|---|
| 3,375,243 | 3/1968 | Nevin et al. | 536/18.6 |
| 4,713,447 | 12/1987 | Letton | 536/18.6 |
| 4,748,158 | 5/1988 | Biermann et al. | 514/25 |
| 4,889,925 | 12/1989 | Schmid et al. | 536/18.6 |

*Primary Examiner*—John Kight
*Assistant Examiner*—Everett White
*Attorney, Agent, or Firm*—Wayne C. Jaeschke; John E. Drach; Steven J. Trzaska

[57] ABSTRACT

The aliphatic primary alcohols are reacted with a glycose, more especially glucose, in the presence of an acidic catalyst in certain process steps so that particularly light-colored and alkali-stable alkyl glucosides are obtained after a subsequent, compulsory bleaching step, which represents an improvement over known direct synthesis processes. The process may be carried out both on a laboratory scale and also on an industrial production scale.

22 Claims, No Drawings

PROCESS FOR THE DIRECT PRODUCTION OF ALKYL GLYCOSIDES

This application is a continuation, of application Ser. No. 08/112,838 filed on Aug. 26, 1993, now abandoned, which is a continuation of Ser. No. 07/671,733 filed on Jun. 5, 1991, now abandoned.

This invention relates to a further development of the process for the direct production of surface-active alkyl glycosides, i.e. the acetals of sugars and aliphatic alcohols, by direct acid-catalyzed reaction of the alcohols with the sugars with elimination of water.

The name alkyl glycosides is used in the following for the reaction products of sugars and aliphatic alcohols, the sugar component being selected from any of the aldoses or even ketoses in the broadest sense hereinafter referred to as glycoses, including for example glucose, fructose, mannose, galactose, talose, gulose, allose, altrose, idose, arabinose, xylose, lyxose and ribose. The aldoses are preferably used by virtue of their better reactivity. Among the aldoses, glucose is particularly suitable because it is readily obtainable and available in industrial quantities. The alkyl glycosides produced with particular preference by the process according to the invention are therefore the alkyl glucosides. The term alkyl in alkyl glycoside in the broadest sense encompasses the residue of an aliphatic alcohol of any chain length, preferably a primary aliphatic alcohol and, more preferably, a fatty alcohol obtainable from natural fats, so that the term encompasses saturated and unsaturated residues and mixtures thereof, including those of different chain length in admixture. The names alkyl oligoglycoside, alkyl polyglycoside, alkyl oligosaccharide and alkyl polysaccharide apply to those alkylated glycoses in which an alkyl radical in the form of the acetyl is attached to more than one glycose residue, i.e. to a poly- or oligosaccharide residue. These names are regarded as synonymous with one another. Accordingly, an alkyl monoglycoside is the acetal of a monosaccharide. Since mixtures are generally obtained in the acid-catalyzed reaction of sugars and fatty alcohols, the name alkyl glycoside is used in the following both for alkyl mono-glycosides and also for alkyl poly(oligo)glycosides and, in particular, mixtures thereof, including any secondary components, providing the structural differences are not crucial.

The surface-active alkyl glycosides have been known for more than 50 years as ingredients of detergents. Thus, Austrian patent 135 333 describes the production of lauryl glucoside and acetyl glucoside from acetobromoglucose and the particular fatty alcohol in the presence of a base. Direct synthesis from glucose and lauryl alcohol using hydrogen chloride as an acidic catalyst is also described therein. According to the teaching of German patent 611 055, alkyl glucosides are produced from pentaacetyl glucose and the fatty alcohol in the presence of anhydrous zinc chloride. The maltosides and lactosides of aliphatic alcohols containing more than 8 carbon atoms and their use as surfactants are known from German patent 593 422. For example, it is stated in this publication that cetyl maltoside improves the washing effect of soap, which at that time was the most important surfactant, which is explained by the effect of cetyl maltoside as a lime soap dispersant. The sixties and seventies saw several proposals for the improved production of alkyl glycosides either by direct reaction of the glycose, generally glucose, with an excess of the alcohol and an acid as catalyst or using a lower alcohol or glycol as solvent and reactant to a primary reaction product, from which the surface-active alkyl glycoside is obtained by transacetalization with the relatively long-chain alcohol. U.S. Pat. No. 3,450,690 (Gibbons et al) describes a process for the direct synthesis of alkyl glucosides, albeit with $C_{1-8}$ alkanols, secondary synthesis products or impurities producing unwanted discoloration in the alkaline medium being removed from the crude product by treatment of the crude product in aqueous solution while heating with inorganc or organic bases such as, for example, sodium hydroxide, sodium methylate, calcium hydroxide, barium hydroxide, barium methylate or strongly basic amines. The acidic catalyst (for example sulfuric acid) not only is said to be neutralized, an alkaline pH value of at least 8 is actually adjusted. After heating to temperatures of 50° to 200° C., the impurities precipitate. They are then filtered off and the alcohol excess is distilled off. The aqueous solution in this literature reference is understood to be the mixture of the excess of the alcoholic reactant and the water formed during the reaction. In some Examples, the excess alcohol (ethanol) is removed and partly replaced by water. After the insoluble precipitate has been filtered off, the filtrate is lightened by treatment with active carbon. Bleaching with hydrogen peroxide is also mentioned as an equivalent measure to the treatment with active carbon. Calcium hydroxide is preferably used as the base. U.S. Pat. No. 3,839,318 (Mansfield et al) describes a process for the direct glucosidation of long-chain alcohols in which the reaction rate is controlled through the reaction temperature and the catalyst concentration in such a way that the water of reaction formed is quickly removed from the reaction mixture by azeotropic distillation. A hydrocarbon, for example hexane or heptane, is preferably added as solvent to facilitate the rapid azeotropic distillation of the water. The reaction mixture is then neutralized with an aqueous solution of sodium hydroxide (alkaline pH values may even be adjusted in this neutralization step). The excess alcohol is then removed in the usual way by distillation. Conversion of the reaction product into an aqueous paste and bleaching of this paste with sodium perborate are also described.

According to European patent application 132 046 (Procter & Gamble, Letton) the acidic catalyst in a direct synthesis process is neutralized with an organic base, a narrow pH range in the vicinity of the neutral point (pH 6.6 to 7 and preferably 6.7 to 6.8) being adjusted. The organic base used is either an alkali (Na, K, Li) or alkaline earth (Ba, Ca) or aluminium salt of a weak low molecular weight acid, for example sodium acetate, or a corresponding alcoholate, for example sodium ethylate.

European patent application 96 917 (Procter & Gamble, Farris) describes an improved process for acid-catalyzed direct synthesis, in which a monosaccharide, preferably glucose, is added continuously or in portions to a mixture of fatty alcohol and catalyst at 80° to 150° C. so that never more than 10% unreacted monosaccharide is present in the reaction mixture.

According to European patent application 77 167 (Rohm & Haas, Arnaudis), the color quality of surface-active alkyl glycosides can be improved by using a typical acidic catalyst together with an acidic reducing agent from the group consisting of phosphorous acid, hypophosphorous acid, sulfurous acid, hyposulfurous acid, nitrous acid and/or hyponitrous acid or the corresponding salts in the production of the alkyl glycosides.

According to the teaching of European patent application 102 558 (BASF, Lorenz et al), light-colored $C_{3-5}$ alkyl glucosides are obtained by production in the presence of an acidic catalyst and at least equivalent quantities of an alkali metal salt of a boric acid, preferably sodium perborate.

Finally, it is proposed in European patent application 165 721 (Staley, McDaniel et al) to treat an aqueous solution of a surface-active alkyl polyglucoside first with an oxidizing agent, preferably with a hydrogen peroxide solution, and then with a sulfur dioxide source, for example an aqueous solution of sodium bisulfite. The products thus obtained are said to be color-stable, even after prolonged storage.

In the production of surfactant raw materials, efforts have always been made to obtain substantially colorless products. Colored impurities or initially colorless products which discolor in storage are often classified as low-grade or unuseable unless aesthetically satisfactory mixtures can be obtained with them. Color stability in alkaline medium is a particularly important factor in the further processing of surfactant raw materials. Although industrial surfactant raw materials can often be converted into light-colored products, which remain light-colored even in storage and in alkaline medium, by bleaching, for example with aqueous hydrogen peroxide solutions, this bleaching treatment cannot be successfully applied to hitherto known surface-active alkyl glycosides because even apparently lightened products reassume a dark-brown coloration when, after bleaching, they are treated with aqueous alkali at elevated temperature. Known processes for the production of alkyl glycosides, which also seek to improve color quality and stability in storage, are attended by the disadvantage that either additional chemical agents have to be added during the production process or the reaction product itself has to be aftertreated with such chemical agents. The object of the present invention is to provide a new process for the production of surface-active alkyl glycosides by so-called direct synthesis in which a suitable choice and configuration of the process parameters ensures that the product bleached in the final step of the process retains its lightness during storage and further processing, even under alkaline conditions at elevated temperature. Another object of the invention is to arrange the process steps in such a way that a minimum of chemical reactants and a minimum of process measures are sufficient. A final object of the invention is to select the process steps in such a way that the process can be carried out on an industrial scale without any scaling-up problems and is suitable for the production of surface-active alkyl glycosides in such quantities that the end product can be processed as a surfactant raw material in the detergent industry.

It has now been found that these and other objects can be achieved by a novel combination of both known and also new process features into a new direct synthesis process.

Accordingly, the present invention relates to a process for the direct production of alkyl glycosides by acetalization of higher aliphatic primary alcohols with glycoses, particularly glucose, in the presence of an acidic catalyst, rapid removal of the water of reaction, neutralization of the catalyst with a base, removal of the alcohol excess by distillation and conversion of the reaction product into an aqueous paste and bleaching of this paste, the aliphatic alcohol being used in a molar excess to the glycose and the formation and removal of the water of reaction taking place in vacuo and reaction temperatures above 80° C. being applied. The process is characterized in that a) mixtures of aliphatic primary alcohol, glycose and acidic catalyst are prepared and reacted at elevated temperature, either
  (i) part of the alcohol being initially introduced with the catalyst, the mixture being heated and a heated suspension of the glycose in the remaining quantity of alcohol being added continuously or in portions to the alcohol/catalyst mixture and the water of reaction formed being distilled off in vacuo, or
  (ii) a mixture of the entire alcohol and the glycose being initially introduced, heated and the acidic catalyst being added to the heated mixture, a vacuum subsequently being applied and the mixture being further heated until the reaction begins and the water of reaction formed being distilled off,
b) the mixing ratios are selected so that the molar ratio of glycose to aliphatic alcohol is from 1:2 to 1:10 and preferably from 1:3 to 1:6,
c) the reaction mixture is kept at that temperature and under that reduced pressure, preferably while mixing, until the water of reaction has been completely removed,
d) the reaction mixture is subsequently cooled to approximately 90° C., after which an organic or inorganic basic alkali, alkaline-earth or aluminium or alkali/aluminium compound is added in such quantities that, over and above the neutralization of the acidic catalyst, a pH value of at least 8 and preferably in the range from 8 to 10 is established and normal pressure is preferably only established thereafter,
e) the excess alcohol is distilled off from the alkaline mixture in vacuo, preferably without preliminary filtration, to a value below 5% by weight of the reaction product by any of the methods known per se which do not damage the reaction product and
f) the mixture is subsequently cooled to approximately 105° to 130° C. and a 30 to 70% paste is produced by addition of water and is stirred for about 0.1 to 5 hours at approximately 80° C. by the addition, preferably in portions, of active oxygen compounds, preferably hydrogen peroxide, measures optionally being taken by addition of alkali, preferably sodium hydroxide, to ensure that the pH value remains at 8 to 10 during this bleaching process.

The reaction product is obtained in the form of a colorless to yellowish aqueous paste. It has surprisingly been found that this paste retains its original color quality substantially unchanged during storage and, above all, even during further processing in alkaline medium. The color stability of the product is determined by a simple test. To this end, a sample of the product is mixed with water to form an approximately 50% paste, after which concentrated sodium hydroxide is added at normal temperature so that a pH value of approximately 12 to 13 is adjusted. The paste is then heated for 30 minutes to 100° C. In the mixtures containing process products, little or no color change occurred after this treatment. The color values of the products were determined by the KLETT method (5% solution in water/isopropyl alcohol 1:1, 1 cm cell, blue filter). Long-term storage tests of the paste-form product under typical conditions and further processing of the stored product above all to detergents and cleaning prepartions and the alkaline conditions which this involves can be reliably simulated by this test method. The end products of the process preferably have Klett values of less than 35.

The glycose preferably used in the process according to the invention is glucose. Commercially available glucose often contains 1 mol water of crystallization. This glucose containing water of crystallization may readily be used, although the water of crystallization present is also best removed from the reaction medium by thermal measures, preferably before contact with the catalyst. However, since anhydrous glucose is also commercially available in large quantities, it is preferred to use anhydrous glucose in the form of a finely divided powder.

Suitable catalysts are, generally, any acidic compounds, including the so-called Lewis acids which catalyze the acetalization reaction between the fatty alcohol and the sugar molecule. Of these catalysts, sulfuric acid, phosphoric acid, aliphatic and/or aromatic sulfonic acids, preferably p-toluenesulfonic acid, and the sulfoacidic ion exchanger resins are particularly suitable. Preferred catalysts for the process according to the invention are sulfuric acid and, above all, p-toluenesulfonic acid which has a less corrosive effect on appliances and pipes of steel. Acidic ion exchangers are also suitable in the present case providing the catalyst is separated off after acetalization of the glycose. In such a case, a suitable basic compound is preferably added after separation of the acidic exchanger resin to adjust the mixture to a pH of 8 to 10.

The conditions under which the three components, aliphatic alcohol, glycose and catalyst, are mixed may be varied within wide limits. Thus, in one variant of the process according to the invention, it is possible initially to introduce a mixture of the total quantities of all three components and to initiate the reaction by heating. In another variant, part of the alcohol is initially introduced with the catalyst and a heated suspension of the glycose in the remaining quantity of alcohol is gradually added. Addition in portions is preferred for laboratory-scale batches while continuous addition is preferred for industrial batches. The time intervals at which the individual portions are added are preferably selected so that a substantially clear phase is always present, i.e. the quantity of unreacted glycose in the reaction mixture is kept very small, i.e. no more than 10%. The mixing ratio of glycose to aliphatic alcohol may also be varied within wide limits. It is possible in this way to control the degree of distribution between alkyl monoglycoside and alkyl oligoglycosides in the reaction product.

In the case of laboratory-scale batches and, above all, in the case of industrial-scale batches, it has been found that the fine dispersion of the glycose in the alcohol, particularly the long-chain alcohol, has a considerable positive effect on the quality of the reaction product. The fine dispersion is achieved by intensively mixing the finely powdered glycose, above all the glucose, optionally after fine grinding, with the alcohol. For laboratory batches, it has proved to be suitable to use a high-speed standard laboratory stirrer or even ultrasonication for this purpose. For industrial batches, inline mixers, for example a stator/rotor mixer, are advantageously used for the fine dispersion. This fine-dispersion measure has the desired additional effect of heating the suspension.

A vacuum of approximately 10 to 50 mbar is applied during formation and removal of the water of reaction. The mixture is heated and preferably continuously mixed during the reaction which, in the case of laboratory-scale batches, is done by simple stirring whereas, in the case of industrial-scale batches, the mixture is heated and mixed by pump circulation through an external liquid circuit incorporating a heat exchanger. During application of the heat required to maintain the reaction temperature, it is essential that there be only a slight temperature difference between the wall of the reactor and the reaction mixture to avoid overheating. To establish this slight temperature difference, it is sufficient for laboratory-scale batches to use a standard oil bath with a thermostat and, at the same time, vigorously to stir the reaction mixture. In the case of industrial-scale batches, it has proved to be of particular advantage to apply the heat through an external circuit preferably consisting of a pump and a heat exchanger. To this end, part of the reaction mixture is continuously removed through a pipe, heated in the heat exchanger and returned to the reactor. In this way, it is possible to avoid high reactor wall temperatures, i.e. above 125° C., and hence to prevent the color values of the end product from being adversely affected by temperature.

The aliphatic primary alcohols reacted in accordance with the invention may basically have any chain lengths, i.e. from 1 to about 30 carbon atoms. To obtain surface-active reaction products which may be used as surfactant raw materials in detergents and cleaning prepartions, it is preferred to use aliphatic primary alcohols containing from 8 to 20 carbon atoms and more especially from 12 to 18 carbon atoms. These higher aliphatic alcohols are preferably produced from industrial fatty compounds. However, synthetic primary alcohols, for example the so-called oxoalcohols, may of course also be used in the process according to the invention.

Where the portion variant of the process is used, 30 to 70% by weight of the alcohol is preferably initially introduced together with the catalyst, the mixture is heated to 100° to 120° C. and the glycose is subsequently added, preferably continuously in vacuo, in the form of a suspension in the heated remaining quantity of alcohol. The water of reaction formed is continuously distilled off. The reaction is regarded as over when no more water of reaction is eliminated. To determine the quantity of water of reaction and thus to ascertain the end of the reaction, the water may be collected, for example, by freezing in a cold trap. Accordingly, with predetermined quantities of mixture and reaction conditions, the reaction time can be reliably determined without the water of reaction having to be collected and measured each time.

In the equally preferred variant where the total quantity of mixture is introduced, the mixture of alcohol and glycose is preferably initially introduced and then heated with stirring, i.e. to a sump temperature of approximately 80° C., after which the acidic catalyst is added to the heated mixture. A vacuum is then applied and the mixture further heated to approximately 100° to 120° C., the water of reaction formed being distilled off.

Since, as already mentioned, the alcohols may be used in a wide chain-length range in the process according to the invention, the degree of vacuum may also be adjusted so that the boiling point of the alcohol is reduced by at least 30° C. For the reaction of the long-chain $C_{12-18}$ fatty alcohols, the vacuum is preferably adjusted to a value of 10 to 50 mbar.

The higher aliphatic, primary $C_{12-18}$ alcohols particularly important as the alcohol component are preferably saturated and, in particular, linear alcohols of the type obtainable on an industrial scale by hydrogenation of native fatty acids. Typical representatives of the higher aliphatic alcohols which may be used in the process according to the invention are, for example, the compounds n-dodecyl alcohol, n-tetradecyl alcohol, n-hexadecyl alcohol, n-octadecyl alcohol, n-octyl alcohol, n-decyl alcohol, undecyl alcohol, tridecyl alcohol. Since the fatty alcohols preferably emanate from natural fats, mixtures of technical fatty alcohols are also usually suitable as reactants. Besides the actual fatty alcohols, branched-chain primary alcohols, for example the so-called oxoalcohols, are also suitable for the reaction. Typical oxoalcohols are, for example, the compounds $C_{12-13}$ alkanol with approximately 25% mainly 2-methyl branching (Dobanol 23) and the corresponding $C_{9-11}$ alkanol (Dobanol 91). However, a major advantage of the process is that it can be used in the production of surfactants obtainable exclusively from renewable raw materials.

Suitable basic alkali, alkaline earth or aluminium or alkali/aluminium compounds, which may be organic or inorganic, are, for example, calcium hydroxide, calcium oxide, magnesium hydroxide, magnesium oxide, the zeolites NaA or NaX, preferably in combination with calcium hydroxide, anhydrous sodium carbonate, potassium carbonate, magnesium and calcium carbonate, sodium methylate, sodium ethylate, magnesium methylate, magnesium ethylate, sodium or magnesium propylate or butylate, i.e. the alcoholates of low-boiling alcohols, preferably $C_{1-4}$ alcohols. The particularly preferred inorganic basic compound is magnesium oxide while the particularly preferred organic base is a magnesium alcoholate, more particularly the ethanolate of magnesium. Both the magnesium oxide and the magnesium alcoholate may be partly replaced, i.e. up to half the molecular weight, by powdered sodium hydroxide in equivalent quantities.

One particular feature of the process is that the additions of the basic compounds are controlled in such a way that, over and above neutralization of the acidic catalyst, an excess of the basic compound is present so that the reaction mixture shows a distinctly basic reaction and, hence, preferably has a pH value in the range from 8 to 10. The pH value is measured in a 10% aqueous/alcoholic emulsion of a sample using a standard pH meter.

The alcohol excess is distilled off without damaging the reaction product by a suitable vacuum distillation method. The distillation process is carried out under a vacuum of 0.01 to 1 mbar. Basically, the product-preserving distillation also includes the establishment of a low sump temperature, by which is meant the temperature of the boiling mixture. In the present case, however, it has surprisingly been found to be of advantage to heat the reaction mixture to a sump temperature in the range from 160° to 180° C. and more especially in the range from 160° to 170° C., irrespective of whether a value as high as this is necessary in view of the vacuum applied for distilling off the excess alcohol. Although a sump temperature as high as this initially leads directly to a crude product of poor color quality, it has unexpectedly been found that precisely those products which have been treated at the high sump temperature have a lighter color and better alkali stability in the above-described test after bleaching than products which have been treated at lower sump temperatures and which have an apparently better color quality before bleaching. Accordingly, another important feature of the process is that, during the process step in which the alcohol excess is removed, the reaction mixture is heated in a high vacuum to the high sump temperature of approximately 160° to 180° C., even if this high sump temperature is not necessary for removal of the alcohol excess by distillation, which is the case with the shorter-chain fatty alcohols.

For the distillation of laboratory batches, typical vacuum distillation units are used to remove the alcohol excess. In the case of industrial-scale batches, the alcohol is preferably distilled off by a two-stage process where the fatty alcohol is one containing from 12 to 20 carbon atoms. In a first stage, the fatty alcohol component is depleted to values of from about 40 to about 20% in a thin-layer evaporator or falling-film evaporator. This first stage is also used to degas the reaction mixture. In a second stage, the fatty alcohol is further depleted to the desired final value in a short-path evaporator or a thin-layer evaporator. Based on the end product, this final value may be below 0.5% by weight where the product is to be substantially free from the fatty alcohol. In cases where the end product is specifically required to contain fatty alcohol, the fatty alcohol content may be adjusted to between 3 and 5% by weight. It has been found that end products of the process containing more than 2% by weight and preferably from 3 to 5% by weight fatty alcohol have certain applicational advantages.

So far as the gentle separation of temperature-sensitive mixtures is concerned, it may generally be said that falling film evaporators and, above all, thin-layer evaporators are particulary suitable for gentle evaporation under reduced pressure, because extremely short residence times at the relatively high temperatures necessary can be achieved in evaporators of this type. In the present case, thin-layer evaporators above all are suitable for removing the excess $C_{10-18}$ fatty alcohol from the alkyl glycoside with particularly good surfactant properties. Thin-layer evaporators are evaporators in which a highly viscous, low-boiling mixture is applied to a heated wall and mechanically distributed thereon by rotating wiping elements. Thin liquid layers or liquid films are thus formed and the film surfaces are continually renewed. The vapors formed flow in countercurrent to the product film and leave the evaporator in the externally arranged condenser. Thin-layer evaporators are generally operated at pressures of only a few mbar and the residence time for the product is only a few seconds. In a two-stage plant, of the type preferably used in the process according to the invention, the first evaporator also acts as a preliminary degassing stage for the evaporator used in the second stage. Gases dissolved in the viscous liquid are thus removed from the liquid during the removal of excess fatty alcohol from the reaction product in the first thin-layer evaporator. The short-path evaporator which is also preferably used as the second evaporator is, in principle, a wiped-film evaporator with a condenser built into the evaporator. These evaporators are suitable for the distillation of high-boiling, temperature-sensitive products in the range from $10^{-1}$ to $10^{-4}$ mbar. In short-path evaporators, as in thin-layer evaporators, the liquid is mechanically distributed over the heating surface by wipers. According to the invention, the excess alcohol is removed to almost any residual contents, which may be below 1%, in the short-path evaporator or thin-layer evaporator as the second stage. The two-stage arrangement of the evaporators provides for high throughputs in conjunction with the specific establishment of the desired residual content of fatty alcohol in the end product. For industrial purposes, thin-layer and short-path evaporators can be dimensioned so that throughputs of up to 300 $kg/m^2$ per hour are readily possible. In principle, the preferred variant of the process according to the invention with the two-stage fatty alcohol depletion plant may also be used in suitable dimensions for working up laboratory-scale mixtures.

The alkyl glycosides produced in accordance with the invention are mixtures consisting essentially of alkyl monoglycoside and the alkyl oligoglycosides, essentially confined here to di- and triglycosides, and small amounts of tetra- and pentaglycosides. The distribution between mono- and oligoglycosides in the end product gives a theoretical degree of oligomerization of from 1 to 5. The process is preferably carried out so that the degree of oligomerization is between 1 and 1.5, the quantity of alkyl monoglycoside, based on the total quantity, of alkyl monoglycoside and alkyl oligoglycoside distinctly exceeding 70% by weight. (For a definition of the degree of oligomerization, see Paul J. Flory, Principles of Polymer Chemistry, Cornell University Press, Ithaca, N.Y., 1953, pages 35 to 37). The total quantity of other secondary constituents is generally below 20% by weight. Of these secondary constituents the fatty alcohol component is variable because it depends upon the intensity of the fatty alcohol distillation process. The quantity of residual alcohol in the end products is adjusted to a preferred range of 0.2 to 5% by weight and more especially 0.5 to 2.5% by weight. The residues of unreacted glycose are below 1%. The contents of polymeric glucose in the end product are from 2 to 20% by weight and preferably from 5 to 20% by weight. The quantities of the neutralization products of acidic catalyst and basic compound and any excess of this basic compound in the end product are between 0.5 and 1.5% by weight.

These quantities are based on the reaction product as its exists immediately after removal of the fatty alcohol excess by distillation. The actual end product of the process is the aqueous paste containing 30 to 60% by weight water which is obtained from the reaction product by treatment with warm water and bleaching with active oxygen compounds, particularly hydrogen peroxide. The quantity of active oxygen compound is generally from 0.2 to 1.5% by weight, expressed as $H_2O_2$ and based on the quantity of product after the removal of alcohol. Since the pH value falls during the bleaching step, a base, for example sodium hydroxide, is added together with the per compound to maintain pH values in the range from 8 to 10. The resulting solution or paste preferably contains the salts emanating from neutralization of the catalyst and the bleaching process which have not been separated off. It has been found that there are many applications in which neither the type nor quantity of these residual salts in the aqueous alkyl glycoside paste is problematical. On the contrary, the compounds in question are in any event typical constituents of typical detergents and cleaning preparations. So far as its pH value is concerned, the paste-form end product of the process is generally left as its accumulates after the bleaching step, i.e. the paste has a pH value in the range from 8 to 10. For special applications, the pH value may be reduced to values around the neutral point by addition of an acidic compound of which the presence is favorable, but at least not harmful, to the application envisaged. Suitable acidic additions are, for example, acidic salts, such as sodium or potassium hydrogen sulfate, inorganic acids, such as sulfuric acid, or organic acids, such as citric acid, or sulfonate or sulfate surfactants in the acid form.

For prolonged storage or prolonged transport of the paste-form reaction product, it can be important effectively to prevent microbial degradation processes. Accordingly, the paste-form reaction product prepared in accordance with the invention best contains a typical quantity of a typical antimicrobial agent which improves stability in storage. The antimicrobial addition consists, for example, of 0.1 to 0.2% by weight glutardialdehyde.

One particularly preferred embodiment of the process for the production of light-colored and color-stable alkyl glycosides by the direct synthesis method is characterized by application of the following cumulative process steps:
1. The glycose, particularly the glucose, is finely dispersed in the alcohol by high-speed stirrers or by other high-performance industrial mixers.
2. The base used to neutralize the acid catalyst, preferably a sulfonic acid, consists completely or predominantly of magnesium oxide.
3. The quantity of base is calculated so that, over and above the actual neutralization, a basically reacting mixture, preferably of pH 8 to 10, is obtained.
4. The reaction mixture is not filtered after the neutralization step.
5. Finally, during removal of the excess alcohol by distillation in vacuo, the reaction mixture is heated to a sump temperature of 160° to 180° C. or the heating temperature in the evaporator of the second stage is brought to about 170° to 180° C.

The high quality of the end product after bleaching is attributable to the cumulative application of these process steps together with the other process steps. This combination of process parameters may also be applied in the same way in other processes for the production of alkyl glycosides, for example in the transacetalization process with butanol or propylene glycol, or in processes where polyglycoses, particularly starch and starch degradation products, are used as starting materials.

EXAMPLES

The process according to the invention is illustrated by the following Examples.

EXAMPLE 1

This Example describes the process according to the invention for the direct synthesis of $C_{12}$ alkyl glucoside on a laboratory scale by the method where a glucose/fatty alcohol suspension is added in portions (slurry variant).

559 g (3 mol) n-dodecanol and 2.2 g (11.2 mmol) p-toluenesulfonic acid were introduced into and heated to between 110° and 114° C. in a 2-liter three-necked flask equipped with a stirrer, dropping funnel and water separation column. A suspension of 180 g (1 mol) anhydrous glucose (Puridex, a product of Cerestar Deutschland GmbH) in another 559 g (3 mol) n-dodecanol was then added in portions, more particularly in 10 portions, at intervals of 5 minutes. A vacuum varying from 10 to 15 mbar was applied before the first addition. The glucose/fatty alcohol suspension had also been heated to around 110° C. before the addition. The water of reaction was removed from the reaction medium through the distillation head and frozen and collected in a cold trap cooled with liquid nitrogen. A total of 19 g water was measured.

Thereafter, the reaction mixture was stirred for another 120 minutes at 110° to 115° C. The reaction mixture was then cooled to 90° C., after which 2.0 g (17.5 mmol) magnesium ethylate were added at normal pressure. The mixture was stirred for 30 minutes. The reaction mixture then had a pH value of 9 to 10. The excess alcohol was distilled off from the reaction flask under a vacuum of 0.1 to 0.01 mbar and at a sump temperature of 120° to 170° C. The quantity of distillate was 976 g; the distillation residue, i.e. the actual product, accumulated in a quantity of 299.1 g. Water and 4.5 g of a 35% $H_2O_2$ solution were added to the residue at a temperature of 90° C. The residue was thus processed with stirring to a 60% paste over a period of 120 minutes. The pH value was monitored during the bleaching process and was kept at pH 9 by addition of 50% NaOH. Product characteristics: hydroxyl value 656; residual fatty alcohol 0.7%; dodecyl monoglucoside 67% by weight; dodecyl diglucoside 16% by weight; dodecyl triglucoside 5%; dodecyl tetraglucoside 2% by weight; dodecyl pentaglucoside 1% by weight; polyglucose 7% by weight; glucose below 1% by weight. Klett values: after bleaching: 20; after the color stability test: 25.

EXAMPLE 2

This Example describes the production of a $C_{12-14}$ alkyl glucoside from anhydrous glucose and a technical fatty alcohol (mixture of approximately 75% by weight dodecanol and approximately 25% by weight tetradecanol) by the so-called batch variant (mixture containing the total quantity of reaction components) on a pilot-plant scale.

25.0 kg (129 mol) of a dodecanol/tetradecanol mixture (Lorol S, Henkel KGaA) and 7.7 kg (43 mol) anhydrous glucose (Puridex) were introduced into a 150 liter stainless steel vessel and heated with stirring to approximately 80° C. 53 g (0.28 mol) p-toluenesulfonic acid were than added. The reaction mixture was then heated to approximately 115° C., a vacuum of approximately 20 mbar being applied at the same time. The reaction mixture was stirred for about 4 hours under these conditions and the water of reaction distilled off in vacuo. The resulting yellowish and cloudy reaction solution was cooled to 90° C., after which 35 g (0.87 mol) magnesium oxide were added under normal pressure, followed by stirring for 30 minutes. A pH value of approximately 10 was measured in the reaction mixture. The alcohol excess was then distilled off under a vacuum of 0.5 to 1 mbar, the sump temperature being increased to 170° C. over a period of 3 hours. Approximately 20 kg fatty alcohol were distilled off during the distillation process which lasted a total of 3 hours and was carried out in the reaction vessel. The distillation residue was an orange-red, clear melt which was cooled to approximately 105° C. and then mixed with deionized water at 70° C. to form an approximately 50% paste. 100 ml 50% sodium hydroxide in one portion and 200 ml 35% hydrogen peroxide in five portions were then added over a period of 2.5 hours. The reaction mixture was then stirred for another 5 hours at 80° C. 18.9 kg of a light yellow transparent paste (49.1% water, pH value 9 to 10) were thus obtained as the reaction product.

Product characteristics: hydroxyl value 694; residual fatty alcohol 1.8%; monoglucoside 51% by weight; diglucoside 16% by weight; triglucoside 6% by weight; tetraglucoside 4% by weight; pentaglucoside 2% by weight; hexaglucoside below 1% by weight; polyglucose approx. 17% by weight; salts below 2% by weight. Klett values: 20/20.

After storage of the product for 6 months, the color values and composition (as determined by gas chromatography) were unchanged.

The color stability of a product produced in accordance with the prior art was determined for comparison. This product had been produced in accordance with Example 6 of U.S. Pat. No. 3,839,318 (Mansfield) using a mixture of dodecanol and tetradecanol. However, the aqueous sodium hydroxide of Example 6 was not used to neutralize the acidic catalyst (sulfuric acid), instead sodium methylate was used as base in accordance with EP 132 046 B1 and the pH value adjusted to 7.0. The product thus obtained had a Klett value of 45 and 125 after the treatment with alkali in the color stability test. After conversion into a 60% paste and bleaching with $H_2O_2$, the Klett values measured 25 (immediately after bleaching, pH value below 7) and 110 (after the color stability test). In a repetition of the experiment, the distillation residue was cooled to only 130° C. The resulting end product had the same characteristics.

EXAMPLE 3

This Example describes the production of $C_{12-14}$ alkyl glucoside on an industrial scale.

Of the total quantity of 1860 kg $C_{12-14}$ fatty alcohol (distribution: dodecanol approx. 75% by weight, tetradecanol approx. 25% by weight), half was processed with 300 kg anhydrous glucose (Puridex) in a 2.5 m$^3$ reactor to form a suspension. The suspension was finely dispersed by means of a stator/rotor mixer, undergoing an increase in temperature to 75° C. in the process. In a second reactor (3.2 m$^3$) with a distillation column and an external liquid circuit consisting of a pump and a heat exchanger, the remaining fatty alcohol and 3.9 kg p-toluenesulfonic acid were heated to 115° C. The reactor was then evacuated to a pressure of 20 to 30 mbar. The glucose/fatty alcohol suspension was then continuously added over a period of 1 hour. A total of 30 kg water was distilled off during this period and an after-reaction time of 2 hours. The heat required to remove the water and to maintain the reaction temperature was introduced into the reaction mixture through the external liquid circuit. The water of reaction was collected in a cooled receiver and measured. On completion of the reaction, the mixture was cooled to 90° C. 2.9 kg magnesium methylate in solid form was then taken in through the external liquid circuit to neutralize the acidic catalyst. Normal pressure was then established.

The reaction mixture was then introduced into a thin-layer evaporator of the Sambay type (0.75 m$^2$ evaporator surface, 8 mbar, approx. 170° C.) and the excess fatty alcohol was removed to a depletion value of approximately 32%. The product kept at 135° C. was low in viscosity and could readily be transferred to a short-path evaporator with a roller wiper of the Leybold KD 75 type. The short-path evaporator was operated under the following conditions: evaporator surface 0.75 m$^2$; operating pressure 0.075 mbar, as measured in the evaporator; heating temperature 170° C.; sump temperature 162° C. Alternatively, a thin-layer evaporator was also used in the second depletion stage in a second batch. In a pressure vessel, approximately 88 kg water at room temperature were added to batches of the product (90 kg) in molten format 150° C. to prepare an approximately 50% paste. 1.3 kg of a 35% $H_2O_2$ solution and 0.9 kg of a 50% NaOH solution were separately added. After stirring for 3 hours at 90° C., the product was cooled to 50° C.

Product characteristics: pH valve 9.5; Klett value 23 (after bleaching) and 26 after the treatment with alkali while heating in the color stability test. Composition of the product (anhydrous): hydroxyl value 650; residual fatty alcohol 3% by weight; alkyl monoglucoside 62.8% by weight; alkyl diglucoside 15.4% by weight; alkyl triglucoside 5.8% by weight; alkyl tetraglucoside 2.5% by weight; alkyl pentaglucoside 1.1% by weight; alkyl hexaglucoside 0.2% by weight; polyglucose 6% by weight; glucose less than 1% by weight; salts less than 2% by weight.

We claim:

1. In a process for the direct production of alkyl glucosides by acetalization of aliphatic primary alcohols having from 1 to about 30 carbon atoms with glucose in the presence of an acidic catalyst, at a temperature of from about 80° C. to about 120° C. with rapid removal of the water of reaction, neutralization of the catalyst with a base, removal of unreacted alcohol by distillation, conversion of the reaction product into an aqueous paste and bleaching of the paste with hydrogen peroxide, the aliphatic alcohol being present in a molar excess to the glucose, the formation and removal of the water of reaction taking place at reaction temperatures above 80° C. under reduced pressure the improvement which comprises:

a) preparing a mixture of said aliphatic primary alcohol, glucose and acidic catalyst and reacting the mixture at a temperature of from about 100° C. to about 120° C. by a method selected from the group consisting of
   (i) mixing a first portion of the alcohol with the catalyst, heating the mixture of alcohol and catalyst and adding a heated suspension of the glucose in a second portion of alcohol to the heated alcohol/catalyst mixture and distilling the water of reaction formed under a reduced pressure of from about 10 to about 15 mbar, or (ii) forming a mixture of the alcohol and the glucose and heating the mixture of alcohol and glucose, adding the acidic catalyst to the heated mixture, applying a reduced pressure of from about 10 to about 15 mbar to the mixture and further heating the mixture and distilling off the water of reaction formed;

b) the molar ratio of glucose to aliphatic alcohol being from 1:2 to 1:10;

c) maintaining the reaction mixture at the reaction temperature and under the reduced pressure, while mixing, to remove the water of reaction to form a reaction mixture comprising unreacted alcohol;

d) cooling the reaction mixture and neutralizing the reaction mixture to a pH in the range of from at least 8 to 10 with an inorganic basic alkali, alkaline-earth, aluminum or alkali/aluminum compound selected from the group consisting of an alkali metal oxide, hydroxide, or carbonate; an alkaline-earth metal oxide, hydroxide, or carbonate; zeolites NaA or NaX;

e) distilling the unreacted alcohol from the alkaline mixture under a reduced pressure of from about 0.01 to about 1.0 mbar with heating to a temperature of from about 160° C. to about 180° C. to form a reaction product with an alcohol content below 5% by weight of the reaction product;

f) cooling the reaction product from about 105° to 130° C.; and g) producing a bleached paste containing 30 to 70% of the reaction product by addition of water and an active oxygen compound with stirring while maintaining the pH at 8 to 10 during the bleaching process.

2. A process of claim 1 wherein the aliphatic primary alcohols contain 8 to 20 carbon atoms.

3. A process of claim 1, wherein a first portion about 30 to 70% by weight, of the alcohol is mixed with the catalyst, and the mixture is heated to about 100° to 120° C. and the glucose is in the form of a heated suspension in the second portion of alcohol.

4. A process of claim 1 wherein a mixture of the entire quantity of alcohol and the glucose is heated, the acidic catalyst is added to the heated mixture, a reduced pressure is applied to the mixture and the mixture is further heated to about 100° to 120° C. and the water of reaction is distilled off.

5. A process of claim 1 wherein the suspension is a dispersion of finely divided glucose in the alcohol.

6. A process of claim 1 wherein the pressure is adjusted so that the boiling point of the alcohol is lowered by at least 30° C.

7. A process of claim 1 wherein the aliphatic primary alcohols are $C_{12-18}$ alcohols.

8. A process of claim 1 wherein the acidic catalyst is present in an amount such that resulting alkali, alkaline earth or aluminum salts can remain in the product.

9. A process of claim 1 wherein the reaction mixture is neutralized with magnesium oxide.

10. A process of claim 1 wherein after neutralization, the basic reaction mixture is heated under a reduced pressure to distill off the unreacted alcohol, to a sump temperature of from 160° to 180° C.

11. A process of claim 1, comprising application of the following cumulative process steps:
1. dispersing the glucose in the alcohol by high-performance industrial mixers;
2. neutralizing the acid catalyst;
3. not filtering the reaction mixture after the neutralization step;
4. heating the reaction product, during removal of the excess alcohol by distillation to a temperature of 160° to 180° C.

12. An alkyl glucoside product of the process of claim 1, having a degree of oligomerization in the range from 1 to 5 and the quantity of alkyl monoglycoside, based on the total quantity of alkyl monoglycoside and alkyl oligoglycoside, is above 70% by weight.

13. The product of claim 12, wherein the quantity of excess alcohol, based on the anhydrous product, is between 0.2 and 5% by weight.

14. The product of claim 12 comprising an aqueous paste containing 30 to 60% by weight water which contains the salts from neutralization of the catalyst and from the bleaching process.

15. A process of claim 1 wherein the glucose is reacted with the alcohol at a temperature in the range of from about 100° C. to about 120° C. and the ratio of glucose:alcohol introduced into the reaction mixture is from about 1:3 to about 1:6.

16. A process of claim 15 wherein the alcohol has from 12 to 18 carbon atoms.

17. A process of claim 16 wherein the active oxygen compound is hydrogen peroxide and the reaction product is stirred with the hydrogen peroxide at a temperature in the range of about 80° C. for from 0.1 hours to about 5 hours.

18. A process of claim 15 wherein the reaction is carried out under a pressure of from about 10 to about 50 mbar.

19. A process of claim 18 wherein the alcohol is a linear alcohol.

20. A process of claim 1 wherein the reaction mixture is cooled to about 90° C. and neutralized with a basic magnesium compound to a pH in the range of 8 to about 10.

21. A process of claim 1, wherein the acid catalyst comprises at least one member selected from the group consisting of sulfuric acid, phosphoric acid, aliphatic sulfonic acid and aromatic sulfonic acid present in an amount of from 0.005 to 0.02 moles per mole of glucose.

22. A process of claim 1 wherein the unreacted alcohol is distilled off to a sump temperature of from about 170° to about 180° C.

* * * * *